United States Patent
Marcovecchio et al.

(10) Patent No.: US 6,512,951 B1
(45) Date of Patent: Jan. 28, 2003

(54) DELIVERY OF ATRIAL DEFIBRILLATION SHOCK BASED ON ESTIMATED QT INTERVAL

(75) Inventors: Alan F. Marcovecchio, Minneapolis, MN (US); Milton M. Morris, Minneapolis, MN (US); Steven D. Girouard, Woodbury, MN (US); Douglas J. Lang, Arden Hills, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 54 days.

(21) Appl. No.: 09/661,875

(22) Filed: Sep. 14, 2000

(51) Int. Cl.$^7$ ................................. A61N 1/39
(52) U.S. Cl. ........................................ 607/5
(58) Field of Search ................. 600/508, 509, 600/513, 515, 516, 518, 519, 521, 547; 607/4–6

(56) References Cited

U.S. PATENT DOCUMENTS

| | | | |
|---|---|---|---|
| RE30,387 E | * 8/1980 | Denniston et al. | 607/6 |
| 5,042,480 A | 8/1991 | Hedin et al. | 128/419 PG |
| 5,207,219 A | 5/1993 | Adams et al. | 128/419 D |
| 5,282,836 A | 2/1994 | Kreyenhagen et al. | 607/4 |
| 5,395,373 A | 3/1995 | Ayers | 607/8 |
| 5,411,524 A | 5/1995 | Rahul | 607/4 |
| 5,480,413 A | 1/1996 | Greenhut et al. | 607/14 |
| 5,486,198 A | * 1/1996 | Ayers et al. | 600/518 |
| 5,545,182 A | 8/1996 | Stotts et al. | 607/5 |
| 5,554,174 A | 9/1996 | Causey, III | 607/5 |
| 5,560,370 A | * 10/1996 | Verrier et al. | 128/925 |
| 5,584,864 A | 12/1996 | White | 607/5 |
| 5,591,215 A | 1/1997 | Greenhut et al. | 607/14 |
| 5,674,250 A | 10/1997 | de Coriolis et al. | 607/7 |
| 5,713,930 A | 2/1998 | van der Veen et al. | 607/25 |

(List continued on next page.)

FOREIGN PATENT DOCUMENTS

| | | | |
|---|---|---|---|
| WO | 93/02746 | 2/1993 | A61N/1/368 |
| WO | 98/48891 | 11/1998 | A61N/1/362 |

OTHER PUBLICATIONS

*Metrix Model 3020 Implantable Atrial Defibrillator*, Physician's Manual, InControl, Inc., Redmond, WA, pp. 4–24 – 4–27, (1998).

Ayers, G.M., et al., "Ventricular Proarrhythmic Effects of Ventricular Cycle Length and Shock Strength in a Sheep Model of Transvenous Atrial Defibrillation", *Circulation, 89* (*1*), pp. 413–422, (Jan. 1994).

Greenhut, S., et al., "Effectiveness of a Ventricular Rate Stabilization Algorithm During Atrial Fibrillation in Dogs", *Pace Abstract*, Abstract No. 60, 1 p., (1996).

Wittkampf, F., et al., "Rate Stabilization by Right Ventricular Pacing in Patients with Atrial Fibrillation", *Pace, 9*, pp. 1147–1153, (1986).

*Primary Examiner*—Kennedy Schaetzle
*Assistant Examiner*—Kristen Droesch
(74) *Attorney, Agent, or Firm*—Schwegman, Lundberg, Woessner & Kluth, P.A.

(57) ABSTRACT

An apparatus and method for delivering electrical shock therapy in order to treat atrial tachyarrhythmias such as fibrillation is disclosed. In accordance with the method, atrial defibrillation shocks are delivered synchronously with an R wave if the current R-R interval meets one or more safety criteria so as to be considered shockable. A shockable R-R interval may be defined as one that exceeds the previous QT interval by a specified therapy margin. In one embodiment, the previous QT interval is estimated based upon the measured preceding R-R interval.

16 Claims, 2 Drawing Sheets

U.S. PATENT DOCUMENTS

| | | | | |
|---|---|---|---|---|
| 5,776,164 A | | 7/1998 | Ripart | 607/5 |
| 5,782,887 A | * | 7/1998 | van Krieken et al. | 607/25 |
| 5,814,081 A | | 9/1998 | Ayers et al. | 607/5 |
| 5,840,079 A | | 11/1998 | Warman et al. | 607/4 |
| 5,853,426 A | | 12/1998 | Shieh | 607/5 |
| 5,865,838 A | | 2/1999 | Obel et al. | 607/5 |
| 5,893,882 A | | 4/1999 | Peterson et al. | 607/14 |
| 5,968,079 A | | 10/1999 | Warman et al. | 607/5 |
| 5,987,354 A | | 11/1999 | Cooper et al. | 607/5 |
| 5,987,356 A | | 11/1999 | DeGroot | 607/5 |
| 5,991,657 A | | 11/1999 | Kim | 607/5 |
| 5,999,850 A | | 12/1999 | Dawson et al. | 607/4 |
| 6,047,210 A | | 4/2000 | Kim et al. | 607/4 |
| 6,081,745 A | | 6/2000 | Mehra | 607/4 |
| 6,081,746 A | | 6/2000 | Pendekanti et al. | 607/5 |
| 6,081,747 A | | 6/2000 | Levine et al. | 607/9 |
| RE36,765 E | | 7/2000 | Mehra | 607/4 |
| 6,085,116 A | | 7/2000 | Pendekanti et al. | 607/5 |
| 6,091,988 A | | 7/2000 | Warman et al. | 607/5 |
| 6,246,909 B1 | | 6/2001 | Ekwall | 607/9 |
| 6,249,699 B1 | | 6/2001 | Kim | 607/4 |
| 6,256,534 B1 | | 7/2001 | Dahl | 607/5 |
| 6,272,380 B1 | | 8/2001 | Warman et al. | 607/5 |

* cited by examiner

DELIVERY OF ATRIAL DEFIBRILLATION SHOCK BASED ON ESTIMATED QT INTERVAL

FIELD OF THE INVENTION

This invention pertains to methods for treating atrial tachyarrhythmias. In particular, the invention relates to an apparatus and method for delivering shock therapy to terminate atrial fibrillation.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include sinus tachycardia, ventricular tachycardia, ventricular fibrillation (VF), atrial tachycardia, and atrial fibrillation (AF). Tachycardia is characterized by a rapid rate, either due to an ectopic excitatory focus or abnormal excitation by normal pacemaker tissue. Fibrillation occurs when the chamber depolarizes in a chaotic fashion with abnormal depolarization waveforms as reflected by an EKG.

An electrical shock applied to a heart chamber (i.e., defibrillation or cardioversion) can be used to terminate most tachyarrhythmias by depolarizing excitable myocardium, which thereby prolongs refractoriness, interrupts reentrant circuits, and discharges excitatory foci. Implantable cardioverter/defibrillators (ICDs) provide this kind of therapy by delivering a shock pulse to the heart when fibrillation is detected by the device. An ICD is a computerized device containing a pulse generator that is usually implanted into the chest or abdominal wall. Electrodes connected by leads to the ICD are placed on the heart, or passed transvenously into the heart, to sense cardiac activity and to conduct the shock pulses from the pulse generator. ICDs can be designed to treat either atrial or ventricular tachyarrhythmias, or both, and may also incorporate cardiac pacing functionality.

The most dangerous tachyarrythmias are ventricular tachycardia and ventricular fibrillation, and ICDs have most commonly been applied in the treatment of those conditions. ICDs are also capable, however, of detecting atrial tachyarrhythmias, such as atrial fibrillation and atrial flutter, and delivering a shock pulse to the atria in order to terminate the arrhythmia. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy.

As aforesaid, an ICD terminates atrial fibrillation by delivering a shock pulse to electrodes disposed in or near the atria. The resulting depolarization also spreads to the ventricles, however, and there is a risk that such an atrial shock pulse can actually induce ventricular fibrillation, a condition much worse than atrial fibrillation. To lessen this risk, current ICDs delay delivering an atrial shock pulse until the intrinsic ventricular rhythm is below a specified maximum rate and then deliver the shock synchronously with a sensed ventricular depolarization (i.e., an R wave). That is, a current R-R interval, which is the time between a presently sensed R wave and the preceding R wave, is measured. If the current R-R interval is above a specified minimum value, the interval is considered shockable and the atrial defibrillation shock pulse is delivered.

Judging a current R-R interval to be shockable or not based solely upon whether it exceeds a single specified minimum value, however, can lead to errors because the period during which the ventricle is vulnerable to fibrillation may not be reflected by the current R-R interval. For example, certain R-R interval sequences, such as a long-short R-R interval sequence, are particularly dangerous for shock timing which thus increases the risk of fibrillation for a given specified minimum interval. In order to lessen this risk, the specified minimum interval value can be increased, but this has the effect of delaying the delivery of atrial defibrillation therapy until the patient's heart rate drops to a rate corresponding to the increased minimum interval value. It is an objective of the present invention to provide an improved method for detecting shockable R-R intervals so as to allow defibrillation shocks to be delivered in a safe and timely manner.

SUMMARY OF THE INVENTION

The present invention is a method and apparatus for delivering atrial defibrillation therapy in which delivery of an atrial defibrillation shock pulse is delivered synchronously with a sensed R-wave if the current R-R interval meets one or more safety criteria so as to be considered shockable. A first criterion defines a shockable R-R interval as one that exceeds the previous QT interval by a specified therapy margin. The previous QT interval may be determined by detecting a T-wave following an R-wave or estimated as a function of the measured preceding R-R interval. A second criterion may be applied that requires, in addition to meeting the first criterion, that a current R-R interval be longer than a specified minimum interval value in order to be considered shockable. A third criterion may also be applied which considers a current R-R interval shockable if it exceeds a specified sufficiently-long interval value irrespective of the length of the preceding R-R interval, where the sufficiently-long interval is longer than the specified minimum interval value.

DETAILED DESCRIPTION OF THE INVENTION

Figure 1:
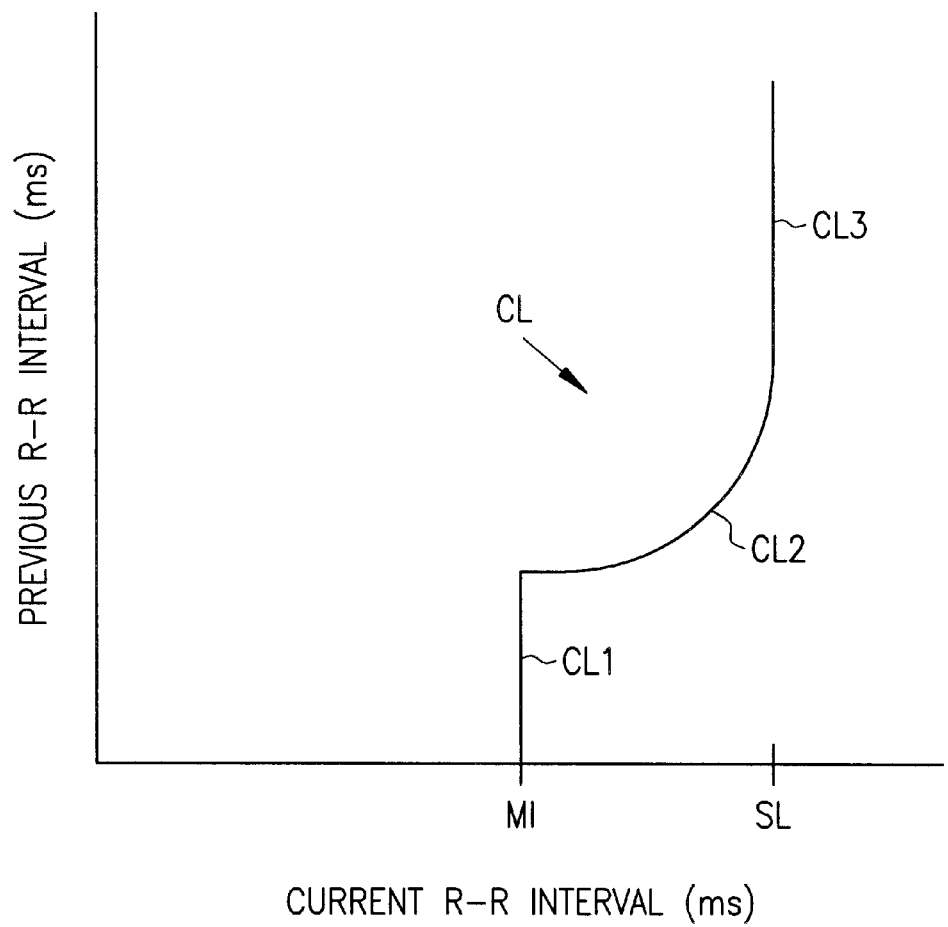
FIG. 1 is a diagram illustrating criteria for determining a shockable R-R interval.

The present invention is a method and apparatus for delivering atrial defibrillation shock therapy. As used herein, atrial defibrillation shock therapy should be taken to mean shock therapy for treating any atrial tachyarrhythmia, such as atrial flutter, as well as atrial fibrillation.

In order to avoid the possible induction of ventricular fibrillation, conventional ICDs deliver atrial defibrillation shocks synchronously with a sensed R wave and after a minimum pre-shock R-R interval. (The R-R interval is the time between the immediately preceding R wave and the presently sensed R wave, and an R wave may be regarded as either a spontaneously occurring depolarization or a ventricular pace.) This is done because the ventricle is especially vulnerable to induction of fibrillation by a depolarizing shock delivered at a time too near the end of the preceding ventricular contraction (i.e., close to the time of ventricular repolarization as indicated by a T wave on an EKG). Delivering the shock synchronously with a sensed R wave thus moves the shock away from the vulnerable period. At a rapid ventricular rhythm, however, the ventricular beats may be so close together that even a synchronously delivered shock may induce ventricular fibrillation. A minimum pre-shock R-R interval is therefore employed to provide a safety margin. Relying solely on the current R-R interval to determine if an R-wave is safe to shock on, however, does not take into account the variability in the length of the vulnerable period due to variations in the length of the QT interval of the preceding beat. This may lead both to shocks being delivered during the vulnerable period and to unnecessary delays in delivering shocks.

In accordance with the present invention, one or more criteria are employed to achieve greater precision in defining a shockable R-R interval than with previous methods. A first criterion is to define a current R-R interval as shockable if it exceeds the QT interval of the previous beat by a specified therapy margin. The QT interval may be measured either by detecting the T-wave of the previous beat or by estimating it as a function of the previous R-R interval. In the latter case, the QT interval as a function of the preceding R-R interval, $QT_{(previos\ RR)}$, may be estimated as a linear function of the previous R-R interval:

$$QT_{(previous\ RR)} = A(R-R_{prev})$$

where A is a defined constant and $R-R_{prev}$ is the measured preceding R-R interval. A more accurate calculation, however, is to use a logarithmic formula of the following form:

$$QT_{(previous\ RR)} = K \ln(R-R_{prev}) - C$$

where K and C are defined constants. A QT interval calculated by this formula has been found to correlate well with measured QT intervals in normal human subjects with K and C set to 166.2 and 715.5, respectively. In subjects with prolonged QT intervals due to Class III antiarrhythmic drugs, bundle branch block, or other disorders, however, it has been found that a more accurate estimate of the QT interval is given by setting K and C to 185.5 and 812.3, respectively. As these are the types of patients for whom implantation of an ICD is typically indicated (i.e., because they are at risk for sudden cardiac death), this is the presently preferred formula for estimating the QT interval in ICD patients. The criterion for judging whether a current R-R interval is safe to shock on then becomes:

$$R\text{-}R\ \text{interval} > 185.5 \ln(R-R_{prev}) - 812.3 + TM$$

where TM is a specified therapy margin (e.g., 60 ms). This criterion thus effectively excludes R-R intervals that are part of a long-short interval sequence from being considered shockable.

A minimum R-R interval criterion may also be employed in addition to the QT interval therapy margin described above. In this embodiment, a current R-R interval is considered shockable if it exceeds the previous QT interval by a specified therapy margin TM and exceeds a specified minimum interval MI. The combined criteria for determining shockability of an R-R interval may then be stated as:

$$R\text{-}R\ \text{interval} > 185.5 \ln(R-R_{prev}) - 812.3 + TM$$

AND $$R\text{-}R\ \text{interval} > MI$$

A third criterion may also be employed that overrides the QT interval criterion if the current R-R interval is sufficiently long. In this embodiment, an R-R interval is considered shockable if it exceeds a specified sufficiently-long interval SL regardless of the length of the previous R-R interval. The combination of all three criteria may then be stated as:

$$((R\text{-}R\ \text{interval} > 185.5 \ln(R-R_{prev}) - 812.3 + TM)\ \text{AND}\ (R\text{-}R\ \text{interval} > MI))$$

OR $$(R\text{-}R\ \text{interval} > SL)$$

where SL is greater than MI.

FIG. 1 graphically illustrates the combination of the three criteria by means of a Poincare map. The vertical axis represents the previous R-R interval, while the horizontal axis represents the current R-R interval. Points on the right and left sides of the criterion line CL are considered in the shockable and non-shockable domains, respectively. Thus a current R-R interval will be considered shockable if the previous RR interval is such that the point lies to the right of the criterion line CL. The criterion line is divided into three segments, labeled CL1 through CL3, which represent the three criteria for judging the shockability of an R-R interval described above. The CL1 segment is part of a vertical line corresponding to the equation:

$$\text{current}\ R\text{-}R\ \text{interval} = MI$$

The CL2 segment is part of a curve corresponding to the equation:

$$\text{current}\ R\text{-}R\ \text{interval} = K \ln(R-R_{prev}) - C + TM$$

where MI is the specified minimum interval, TM is the specified therapy margin, and K and C are specified constants for the logarithmic equation that estimates a QT interval from the previous R-R interval. In another embodiment, the CL2 segment is a straight line with a specified slope. The CL3 segment is part of a vertical line corresponding to the equation:

$$\text{current}\ R\text{-}R\ \text{interval} = SL$$

where SL is the specified sufficiently-long interval. Thus for a short previous R-R interval that estimates a short QT interval, the criterion for shockability is dictated by segment CL1 so that only a current R-R interval that exceeds MI is considered shockable. Only when the previous R-R interval becomes long enough so that the sum of the estimated QT interval and the therapy margin TM exceeds MI does segment CL2 come into play in determining shockability. For previous R-R intervals that fall within the CL2 segment, a current R-R interval is considered shockable only if it exceeds the sum of the estimated QT interval and the therapy margin. When the previous R-R interval is long enough so that the sum of the estimated QT interval and the therapy margin TM exceeds the sufficiently-long interval SL, shockability is determined solely by whether or not the current R-R interval exceeds SL as represented by the segment CL3.

Figure 2:
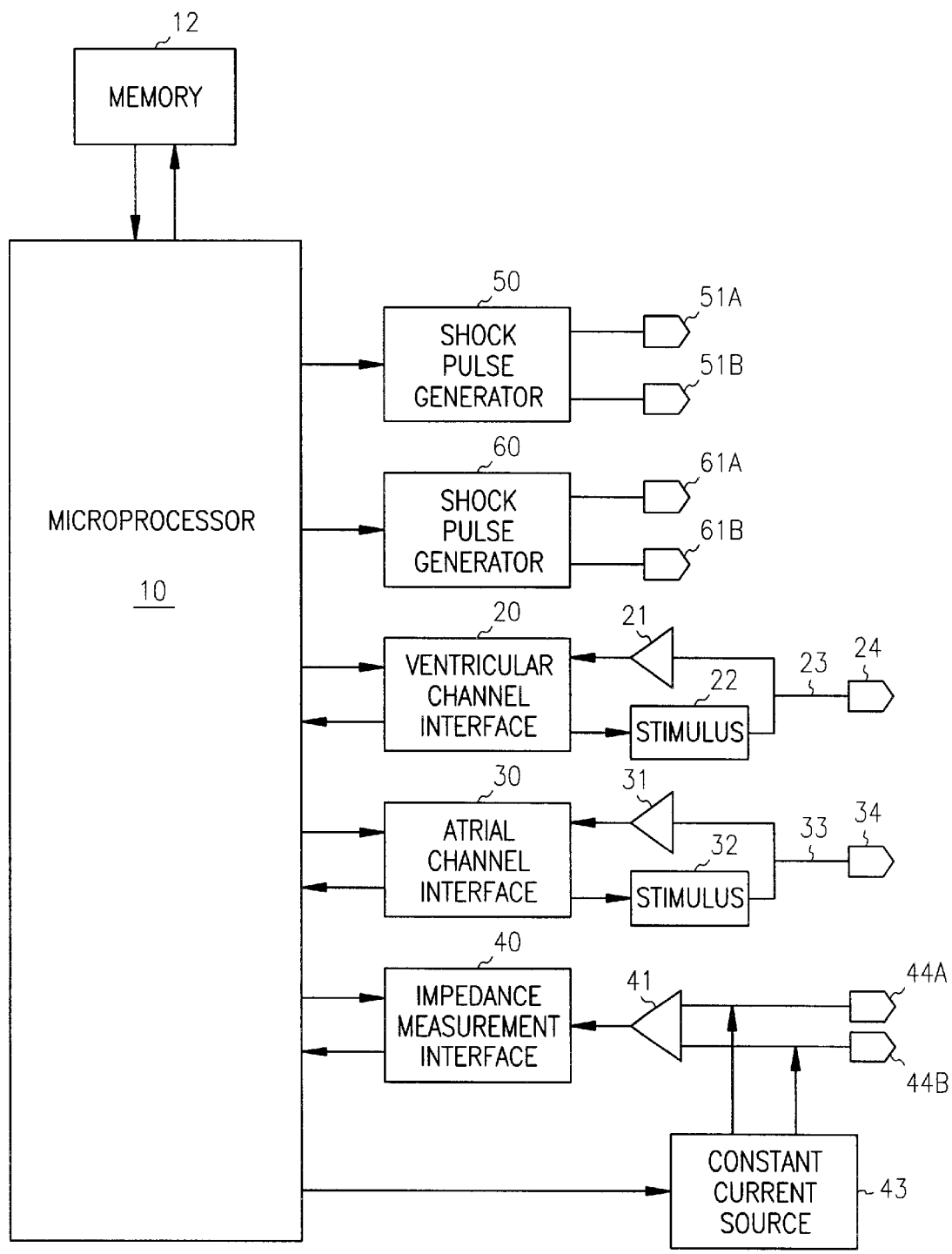
FIG. 2 is a system diagram of an implantable defibrillator.

FIG. 2 is a system diagram of a microprocessor-based implantable cardioverter/defibrillator device for treating atrial tachyarrhythmias that in which the method described above may be implemented. In this device, which also includes a pacemaker functionality, a microprocessor and associated circuitry make up the controller, enabling it to output pacing or shock pulses in response to sensed events and lapsed time intervals. The microprocessor 10 communicates with a memory 12 via a bidirectional data bus. The memory 12 typically comprises a ROM or RAM for program storage and a RAM for data storage. The ICD has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The sensing channels are used to control pacing and for measuring heart rate in order to detect tachyarrythmias such as fibrillation. The ICD detects an atrial tachyarrhythmia, for example, by measuring the atrial rate as well as possibly performing other processing on data received from the atrial sensing channel. A shock pulse generator 50 is interfaced to the microprocessor for delivering shock pulses to the atrium via a pair of terminals 51a and 51b that are connected by defibrillation leads to shock electrodes placed in proximity to regions of the heart. The defibrillation leads have along their length electrically conductive coils that act as electrodes for defibrillation stimuli. A similar shock pulse generator 60 and shock electrodes 61a and 61b are provided to deliver ventricular fibrillation therapy in the event of an induced ventricular fibrillation from atrial shock pulses.

The device in the figure also has the capability of measuring the electrical impedance between electrodes 44a and 44b. A current is injected between the electrodes from constant current source 43, and the voltage between the electrodes is sensed and transmitted to the impedance measurement interface 40 through sense amplifier 41. The impedance measurement interface processes the voltage signal to extract the impedance information therefrom and communicates an impedance signal to the microprocessor. If the electrodes 44a and 44b are disposed in proximity to the heart, the impedance signal can be used to measure cardiac stroke volume. An example of this technique is described in U.S. Pat. No. 5,190,035, issued to Salo et al. and assigned to Cardiac Pacemakers, Inc., which is hereby incorporated by reference.

The device depicted in FIG. 2 can be configured to deliver atrial defibrillation therapy in accordance with the invention as described above by appropriate programming of the microprocessor. Thus, once an episode of atrial fibrillation is detected with the atrial sensing channel, the device prepares to deliver an atrial defibrillation shock. The ventricular rhythm is monitored by measuring the R-R interval associated with each sensed R wave. An atrial defibrillation shock pulse is then delivered synchronously with a sensed R wave if a shockable current R-R interval is measured, where a shockable current R-R interval is defined as an interval that is longer than a preceding QT interval by a specified therapy margin, where the QT interval may be estimated from the previous R-R interval. If a minimum interval criterion is also implemented, only if a sensed R wave also occurs at an R-R interval longer than a specified minimum limit value is sensed R wave considered safe to shock on. If a sufficiently-long criterion is employed, a current R-R interval is considered shockable if it exceeds a specified sufficiently-long interval value irrespective of the length of the preceding QT interval. The device may be programmed so as to specify any of the defined constants that dictate the shockability criteria such as MI, TM, SL, K, and C. The shockability criteria may thus either be based upon population data or tailored to the individual patient.

Because detected R-waves are used to calculate the R-R intervals, it is important for R-waves to be detected as accurately as possible and distinguished from noise. In order to improve the reliability of R-wave sensing, the device of FIG. 2 may be further programmed to use the impedance signal reflecting stroke volume as an indication of ventricular systole. When an R-wave is detected, only if an impedance signal is also detected synchronously therewith is the R-wave considered valid and used to compute an R-R interval. In another embodiment, multiple ventricular electrodes can be used to sense R-waves. For example, two ventricular sensing channels may be used such that a sensed R-wave is considered valid only if it is sensed by both channels. Reliably sensed R-waves can also be used in where T-waves are sensed and used to determine QT intervals. In such embodiments, a reliably sensed R-wave can be used to aid in distinguishing a T-wave from an R-wave by, for example, subtracting the R-wave component from a sensed electrogram to leave only the T-wave component, or causing a T-wave detector to ignore all detected events within a certain time interval before or after a detected R-wave.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An apparatus for delivering atrial defibrillation therapy, comprising:
   an atrial sensing channel;
   a ventricular sensing channel;
   a shock pulse generator for generating atrial defibrillation shock pulses;
   a controller for controlling operation of the shock pulse generator in response to sensed events and for measuring R-R intervals with each sensed R wave; and,
   wherein, after detecting an episode of atrial defibrillation, the controller is programmed to deliver an atrial defibrillation shock pulse synchronously with a sensed R wave if a shockable R-R interval is measured, where a shockable current R-R interval is defined as an interval that is longer than a preceding QT interval by a specified therapy margin; and,
   wherein the controller is programmed such that the preceding QT interval is estimated as a function of a measured preceding R-R interval according to the following formula:

$$QT_{(previous\ RR)} = K\ \ln(R-R_{prev}) - C$$

where $QT_{(previous\ RR)}$ is the estimate of the preceding QT interval, K and C are defined constants, and $R-R_{prev}$ is the measured preceding R-R interval.

2. The apparatus of claim 1 wherein the controller is programmed such that a shockable current R-R interval is further defined as also being longer than a specified minimum interval value.

3. The apparatus of claim 1 wherein the controller is programmed such that a current R-R interval is considered shockable if it exceeds a specified sufficiently-long interval value irrespective of the length of the preceding R-R interval.

4. The apparatus of claim 1 wherein the controller is programmed with K and C defined as approximately 166.2 and 715.5, respectively.

5. The apparatus of claim 1 wherein the controller is programmed with K and C defined as approximately 185.5 and 812.3, respectively.

6. The apparatus of claim 1 wherein the controller is programmed with the specified therapy margin defined as approximately 60.

7. The apparatus of claim 1 wherein the controller is programmed such that a shockable current R-R interval is further defined as also being longer than a specified minimum interval value, and further programmed such that a current R-R interval is considered shockable if it exceeds a specified sufficiently long interval value irrespective of the length of the preceding R-R interval.

8. The apparatus of claim 1 further comprising circuitry for performing an impedance measurement related to cardiac stroke volume by injecting current between two electrodes from a constant current source and wherein R waves are sensed by detecting a depolarization and an impedance signal synchronous therewith that is indicative of ventricular systole.

9. A method for delivering atrial defibrillation therapy, comprising:

detecting an episode of atrial defibrillation;

sensing ventricular depolarizations (R waves) and measuring an R-R interval for each sensed R wave;

delivering an atrial defibrillation shock pulse synchronously with a sensed R wave if a shockable current R-R interval is measured, where a shockable current R-R interval is defined as an interval that is longer than a preceding QT interval by a specified therapy margin; and, wherein the preceding QT interval is estimated as a function of a measured preceding R-R interval according to the following formula:

$$QT_{(previous\ RR)} = K \ln(R-R_{prev}) - C$$

where $QT_{(previous\ RR)}$ is the estimate of the preceding QT interval, K and C are defined constants, and $R-R_{prev}$ is the measured preceding R-R interval.

10. The method of claim 9 wherein a shockable current R-R interval is further defined as also being longer than a specified minimum interval value.

11. The method of claim 9 wherein a current R-R interval is considered shockable if it exceeds a specified sufficiently long interval value irrespective of the length of the preceding R-R interval.

12. The method of claim 9 wherein K and C are defined as approximately 166.2 and 715.5, respectively.

13. The method of claim 9 wherein the specified therapy margin is defined as approximately 60.

14. The method of claim 9 wherein R waves are sensed by detecting a depolarization and an impedance signal synchronous therewith that is indicative of ventricular systole.

15. The method of claim 9 wherein K and C are defined as approximately 185.5 and 812.3, respectively.

16. The method of claim 15 wherein a shockable current R-R interval is further defined as also being longer than a specified minimum interval value, and further wherein a current R-R interval is considered shockable if it exceeds a specified sufficiently long interval value irrespective of the length of the preceding R-R interval.

* * * * *